United States Patent
Fazio et al.

(10) Patent No.: US 12,070,271 B2
(45) Date of Patent: *Aug. 27, 2024

(54) COLOCALIZED DETECTION OF RETINAL PERFUSION AND OPTIC NERVE HEAD DEFORMATIONS

(71) Applicant: THE UAB RESEARCH FOUNDATION, Birmingham, AL (US)

(72) Inventors: Massimo Antonio Fazio, Birmingham, AL (US); Christopher Anthony Girkin, Mountain Brook, AL (US)

(73) Assignee: THE UAB RESEARCH FOUNDATION, Birmingham, AL (US)

( * ) Notice: Subject to any disclaimer, the term of this patent is extended or adjusted under 35 U.S.C. 154(b) by 832 days.

This patent is subject to a terminal disclaimer.

(21) Appl. No.: 16/979,657

(22) PCT Filed: Mar. 13, 2019

(86) PCT No.: PCT/US2019/021984
§ 371 (c)(1),
(2) Date: Sep. 10, 2020

(87) PCT Pub. No.: WO2019/178185
PCT Pub. Date: Sep. 19, 2019

(65) Prior Publication Data
US 2021/0022605 A1    Jan. 28, 2021

Related U.S. Application Data

(60) Provisional application No. 62/642,067, filed on Mar. 13, 2018.

(51) Int. Cl.
*A61B 3/12* (2006.01)
*A61B 3/00* (2006.01)
(Continued)

(52) U.S. Cl.
CPC .......... *A61B 3/1233* (2013.01); *A61B 3/0025* (2013.01); *A61B 3/102* (2013.01);
(Continued)

(58) Field of Classification Search
CPC ..... A61B 3/1233; A61B 3/0025; A61B 3/102; A61B 3/1241; A61B 3/165; A61B 8/10;
(Continued)

(56) References Cited

U.S. PATENT DOCUMENTS 7,798,647 B2    9/2010  Meyer et al.
8,474,978 B2    7/2013  Huang et al.
(Continued)

FOREIGN PATENT DOCUMENTS

EP    2465062    12/2017
JP    2013-508035    3/2013
(Continued)

OTHER PUBLICATIONS

Application No. EP19768545.6, Extended European Search Report, Mailed On Nov. 17, 2021, 10 pages.
(Continued)

*Primary Examiner* — Andrey Shostak
(74) *Attorney, Agent, or Firm* — Kilpatrick Townsend & Stockton LLP

(57) ABSTRACT

Relationships between morphological changes to an eye due to intraocular pressure changes and blood perfusion changes in the retina are determined by colocalizing retinal perfusion data and optic nerve head (ONH) mechanical deformation data. Perfusion changes from intraocular pressure (IOP) changes are determined by colocalizing retinal perfusion data with ONH mechanical deformation data. Optical coherence tomography-angiography (OCT-A) can be used to generate both retinal perfusion data and mechanical deformation data for an imaged volume. A three-dimensional
(Continued)

model (e.g., connectivity map or connectivity model) of the vasculature can be generated from the OCT-A imaging data and used to predict changes in blood perfusion in various areas of the retina due to IOP-induced mechanical deformations.

18 Claims, 7 Drawing Sheets

(51) Int. Cl.
  *A61B 3/10* (2006.01)
  *A61B 3/16* (2006.01)
  *G06T 7/00* (2017.01)
  *A61B 8/10* (2006.01)
(52) U.S. Cl.
  CPC ............ *A61B 3/1241* (2013.01); *A61B 3/165* (2013.01); *G06T 7/0016* (2013.01); *A61B 8/10* (2013.01); *G06T 2207/10101* (2013.01); *G06T 2207/30041* (2013.01); *G06T 2207/30104* (2013.01)
(58) Field of Classification Search
  CPC ............ A61B 3/12; A61B 8/0891; A61B 3/16; G06T 7/0016; G06T 2207/10101; G06T 2207/30041; G06T 2207/30104; G06T 7/0012
  See application file for complete search history.

(56) References Cited

U.S. PATENT DOCUMENTS

| | | | |
|---|---|---|---|
| 9,713,424 | B2* | 7/2017 | Spaide ................. A61B 3/1233 |
| 2013/0165763 | A1 | 6/2013 | Huang et al. |
| 2015/0157205 | A1 | 6/2015 | Buckland et al. |
| 2015/0230708 | A1* | 8/2015 | Wang .................... A61B 5/0066 600/479 |
| 2016/0162630 | A1* | 6/2016 | Studer .................... G16H 50/50 703/11 |
| 2016/0228000 | A1 | 8/2016 | Spaide |
| 2017/0055830 | A1* | 3/2017 | Kotoku ................ A61B 3/0025 |
| 2017/0112377 | A1 | 4/2017 | Shiba et al. |

FOREIGN PATENT DOCUMENTS

| | | |
|---|---|---|
| JP | 2017042443 A | 3/2017 |
| JP | 2017042602 A | 3/2017 |
| JP | 2017077413 A | 4/2017 |
| WO | 2011/047342 | 4/2011 |

OTHER PUBLICATIONS

Bellezza et al., Deformation of the Lamina Cribrosa and Anterior Scleral Canal Wall in Early Experimental Glaucoma, Investigative Ophthalmology & Visual Science, vol. 44, No. 2, 2003, pp. 623-637.

Bellezza, The Optic Nerve Head as a Biomechanical Structure: Initial Finite Element Modeling, Investigative Ophthalmology & Visual Science, vol. 41, 2000, pp. 2991-3000.

Berdahl et al., Cerebrospinal Fluid Pressure is Decreased in Primary Open-angle Glaucoma, Ophthalmology, vol. 115, 2008, pp. 763-768.

Berdahl et al., Intracranial Pressure in Primary Open Angle Glaucoma, Normal Tension Glaucoma, and Ocular Hypertension: A Case-control Study, Investigative Ophthalmology & Visual Science, vol. 49, No. 12, Dec. 2008, pp. 5412-5418.

Burgoyne et al., Premise and Prediction—How Optic Nerve Head Biomechanics Underlies the Susceptibility and Clinical Behavior of the Aged Optic Nerve Head, Journal of Glaucoma, vol. 17, No. 4, Jun.-Jul. 2008, pp. 318-328.

Burgoyne et al., The Anatomy and Pathophysiology of the Optic Nerve Head in Glaucoma, Journal of Glaucoma, vol. 10, 2001, pp. S16-S18.

Burgoyne et al., The Optic Nerve Head as a Biomechanical Structure: a New Paradigm for Understanding the Role of Iop-Related Stress and Strain in the Pathophysiology of Glaucomatous Optic Nerve Head Damage, Progress in Retinal and Eye Research, vol. 24, No. 1, 2005, pp. 39-73.

Cioffi et al., Vasculature of the Anterior Optic Nerve and Peripapillary Choroid, In: Ritch R, Shields, The Glaucomas. Basic Sciences, 1996, pp. 177-197.

Coudrillier et al., Biomechanics of The Human Posterior Sclera: Age- and Glaucoma-related Changes Measured using Inflation Testing, Investigative Ophthalmology & Visual Science, vol. 53, No. 4, 2012, pp. 1714-1728.

Coudrillier et al., Effects of Peripapillary Scleral Stiffening on the Deformation of The Lamina Cribrosa, Investigative Ophthalmology & Visual Science, vol. 57, 2016, pp. 2666-2677.

Downs, Optic Nerve Head Biomechanics in Aging and Disease, Experimental Eye Research, vol. 133, Apr. 2015, pp. 19-29.

Downs et al., Viscoelastic Material Properties of the Peripapillary Sclera in Normal and Early-glaucoma Monkey Eyes, Investigative Ophthalmology & Visual Science, vol. 46, No. 2, Feb. 2005, pp. 540-546.

Downs et al., The Mechanical Environment of the Optic Nerve Head in Glaucoma, Optom Vis Sci., vol. 85, No. 6, Jun. 2008, pp. 425-435.

Eilaghi et al., Effects of Scleral Stiffness Properties on Optic Nerve Head Biomechanics, Annals of Biomedical Engineering, vol. 38, No. 4, Apr. 2010, pp. 1586-1592.

Ethier et al., Effect of Scleral Properties on Optic Nerve Head (ONH) Biomechanics, Investigative Ophthalmology & Visual Science, vol. 46, No. 13, May 2005, pp. 2370-2370.

Fazio et al., Human Scleral Structural Stiffness Increases More Rapidly with Age in Donors of African Descent Compared to Donors of European Descent, Investigative Ophthalmology & Visual Science, vol. 55, Nov. 2014, pp. 7189-7198.

Fazio et al., In vivo optic nerve head mechanical response to intraocular and cerebrospinal fluid pressure: imaging protocol and quantification method, Scientific Reports, 8:12639, 2018, 11 pages.

Feola et al., Deformation of the Lamina Cribrosa and Optic Nerve Due to Changes in Cerebrospinal Fluid Pressure, Investigative Ophthalmology & Visual Science, vol. 58, No. 4, 2017, pp. 2070-2078.

Firsching et al., Venous Ophthalmodynamometry: A Noninvasive Method for Assessment of Intracranial Pressure, Journal of Neurosurgery 93, 2000, pp. 33-36.

Girard et al., In Vivo Optic Nerve Head Biomechanics: Performance Testing of a Three-dimensional Tracking Algorithm, Available Online at: https://doi.org/10.1098/rsif.2013.0459, Journal of the Royal Society, Interface/the Royal Society, vol. 10, 2013, pp. 1-13.

Girard et al., Translating Ocular Biomechanics into Clinical Practice: Current State and Future Prospects, Curr Eye Res, vol. 40, 2015, pp. 1-18.

Girkin et al., Variation in the Three-Dimensional Histomorphometry of the Normal Human Optic Nerve Head with Age and Race: Lamina Cribrosa and Peripapillary Scleral Thickness and Position, Available Online at: https://doi.org/10.1167/iovs.17-21842, Investigative Ophthalmology & Visual Science 58, No. 9, Jul. 2017, pp. 3759-3769.

Golzan et al., Non-Invasive Estimation of Cerebrospinal Fuid Pressure Waveforms by Means of Retinal Venous Pulsatility and Central Aortic Blood Pressure, Annals of Biomedical Engineering, vol. 40, 2012, pp. 1940-1948.

Grytz et al., Age-and Race-Related Differences in Human Scleral Material Properties, Investigative Ophthalmology & Visual Science, vol. 55, No. 2, Dec. 2014, pp. 8163-8172.

Hayreh, Pathogenesis of Cupping of the Optic Disc, British Journal of Ophthalmology, vol. 58, No. 10, 1974, pp. 863-876.

Hou et al., Intracranial Pressure (ICP) and Optic Nerve Subarachnoid Space Pressure (ONSP) Correlation in the Optic Nerve Chamber: the Beijing Intracranial and Intraocular Pressure (iCOP) Study, Brain Research, vol. 1635, Mar. 15, 2016, pp. 201-208.

(56) References Cited

OTHER PUBLICATIONS

Jonas et al., Cerebrospinal Fluid Pressure and Glaucoma, Journal of Ophthalmic & Vision Research, vol. 8, Jul. 2013, pp. 257-263.
Jonas et al., Facts and Myths of Cerebrospinal Fluid Pressure for the Physiology of the Eye, Progress in Retinal and Eye Research, vol. 46, 2015, pp. 67-83.
Mackenzie et al., Vascular anatomy of the optic nerve head, Can J Ophthalmo, vol. 43, 2008, pp. 308.312.
Magnaes et al., Body Position and Cerebrospinal Fluid Pressure. Part 1: Clinical Studies on the Effect of Rapid Postural Changes, Journal of Neurosurgery, vol. 44, No. 6, Jun. 1976, pp. 687-697.
Magnaes, Body Position and Cerebrospinal Fluid Pressure. Part 2: Clinical Studies on Orthostatic Pressure and the Hydrostatic Indifferent Point, Journal of Neurosurgery, vol. 44, 1976, pp. 698-705.
Magnaes, Movement of Cerebrospinal Fluid Within the Craniospinal Space When Sitting Up and Lying Down, Surgical Neurology International, vol. 10, No. 1, 1978, pp. 45-49.
Morgan et al., The Correlation Between Cerebrospinal Fluid Pressure and Retrolaminar Tissue Pressure, Investigative Ophthalmology & Visual Science, vol. 39, No. 8, Jul. 1998, pp. 1419-1428.
Morgan et al., The Influence of Cerebrospinal Fluid Pressure on the Lamina Cribrosa Tissue Pressure Gradient, Investigative Ophthalmology & Visual Science, vol. 36, No. 6, May 1995, pp. 1163-1172.
Munoz et al., Causes of Blindness and Visual Impairment in a Population of Older Americans: the Salisbury Eye Evaluation Study, Archives of Ophthalmology, vol. 118, No. 6, Jun. 2000, pp. 819-825.
International Application No. PCT/US2019/021984, International Preliminary Report on Patentability mailed on Sep. 24, 2020, 10 pages.
International Application No. PCT/US2019/021984, International Search Report and Written Opinion mailed on May 23, 2019, 11 pages.
Quigley et al., Optic Nerve Damage in Human Glaucoma. II. The Site of Injury and Susceptibility to Damage, Archives of Ophthalmology, vol. 99, No. 4, 1981, pp. 635-649.
Quigley, Overview and Introduction to Session on Connective Tissue of the Optic Nerve in Glaucoma. Chapter 2, Kugler Publications, 1995.
Quigley et al., Regional Differences in the Structure of The Lamina Cribrosa and their Relation to Glaucomatous Optic Nerve Damage, Archives of Ophthalmology, vol. 99, No. 1, Jan. 1981, pp. 137-143.
Ren et al., Cerebrospinal Fluid Pressure in Glaucoma: A Prospective Study, Ophthalmology, vol. 117, 2010, pp. 259-266.
Ren et al., Cerebrospinal Fluid Pressure in Ocular Hypertension, Acta Ophthalmologica, vol. 89, 2011, pp. e142-e148.
Ren et al., Trans-lamina Cribrosa Pressure Difference Correlated with Neuroretinal Rim Area in Glaucoma, Graefe's Archive for Clinical and Experimental Ophthalmology, vol. 249, Apr. 1, 2011, pp. 1057-1063.
Sigal et al., Eye-Specific IOP-Induced Displacements and Deformations of Human Lamina Cribrosa, Investigative Ophthalmology & Visual Science, vol. 55, No. 1, Jan. 2014, pp. 1-15.
Sigal et al., Factors Influencing Optic Nerve Head Biomechanics, Investigative Ophthalmology & Visual Science, vol. 46, No. 11, Nov. 2005, pp. 4189-4199.
Sigal et al., Finite Element Modeling of Optic Nerve Head Biomechanics, Investigative Ophthalmology & Visual Science, vol. 45, No. 12, Dec. 2004, pp. 4378-4387.
Sigal et al., IOP-Induced Lamina Cribrosa Deformation and Scleral Canal Expansion: Independent or Related? Investigative Ophthalmology & Visual Science, vol. 52, No. 12, Nov. 2011, pp. 9023-9032.
Sigal et al., IOP-Induced Lamina Cribrosa Displacement and Scleral Canal Expansion: An Analysis of Factor Interactions Using Parameterized Eye-Specific Models, Investigative Ophthalmology & Visual Science, vol. 52, No. 3, Mar. 2011, pp. 1896-1907.
Stockslager et al., System for Rapid, Precise Modulation of Intraocular Pressure, Toward Minimally-invasive in Vivo Measurement of Intracranial Pressure, Available Online at: https://doi.org/10.1371/journal.pone.0147020, Plos One, vol. 11, 2016, pp. 1-15.
Susanna, The Lamina Cribrosa and Visual Field Defects in Open-angle Glaucoma, Canadian Journal of Ophthalmology, vol. 18, 1983, pp. 124-126.
Wang et al., In Vivo 3-Dimensional Strain Mapping Confirms Large Optic Nerve Head Deformations Following Horizontal Eye Movements, Available Online at: https://doi.org/10.1167/iovs.16-20560, Investigative Ophthalmology & Visual Science, vol. 57, 2016, pp. 5825-5833.
Wang et al., In-vivo Effects of Intraocular and Intracranial Pressures on The Lamina Cribrosa Microstructure, PLoS One, vol. 12, 2017, pp. 1-16.
Yang et al., Optic Neuropathy Induced by Experimentally Reduced Cerebrospinal Fluid Pressure in Monkeys, Investigative Ophthalmology & Visual Science, vol. 55, No. 5, 2014, pp. 3067-3073.
Zeimer et al., Archives of Ophthalmology, vol. 107, 1989, pp. 1232-1234.
Zeimer, Biomechanical Properties of the Optic Nerve Head, Glaucoma, 1995, pp. 107-121.
Zeimer et al., Could Glaucoma Damage be due to a Viscoelastic Mismatch Between the Sclera and The Lamina Cribrosa? Journal of Japan Glaucoma Society, vol. 2, 1992, pp. 17-20.
Zhao et al., Age-related Changes in the Response of Retinal Structure, Function and Blood flow to Pressure Modification in Rats, Scientific Reports, vol. 8, 2018, pp. 1-12.
JP Patent Application No. 2021-500018, Notice of Reasons for Rejection, mailed Nov. 29, 2022, 13 pages with English translation.
Wong et al., Focal Structure-Function Relationships in Primary Open-Angle Glaucoma Using OCT and OCT-A Measurements, Investigative Ophthalmology & Visual Science, vol. 61, No. 14, Dec. 2020, pp. 1-10.
Japanese Patent Application No. 2021-500018, Notice of Reasons for Rejection, Mailed Aug. 18, 2023, 19 pages with English translation.
EP Patent Application No. 19768545.6 , Examination Report mailed May 16, 2024, 5 pages.
Japanese Patent Application No. 2021-500018, Notice of Allowance, Mailed Feb. 14, 2024, 4 pages with English translation.

\* cited by examiner

ONH perfusion map at 10 mmHg

ONH Deformations map for an IOP change of 10 mmHG

ONH perfusion map at 20 mmHg

3D Vessel Connectivity Map

ONH Deformations map for an IOP change of 10 mmHG

COLOCALIZED DETECTION OF RETINAL PERFUSION AND OPTIC NERVE HEAD DEFORMATIONS

CROSS REFERENCE TO RELATED APPLICATIONS

The present application claims the benefit of U.S. Provisional Application No. 62/642,067 filed Mar. 13, 2018 and entitled "COLOCALIZED DETECTION OF RETINAL PERFUSION AND OPTIC NERVE HEAD DEFORMATIONS," the disclosure of which is hereby incorporated by reference in its entirety.

TECHNICAL FIELD

The present disclosure relates to ophthalmological tools and techniques generally and more specifically to tools and techniques to measure and analyze the retina.

BACKGROUND

In the field of ophthalmology, various techniques can be used to diagnose ocular conditions, such as glaucoma. Glaucoma and other ocular conditions inflict many individuals. Early detection of various conditions can be important to minimizing negative effects of the condition and providing an opportunity for early treatment. In some cases, intraocular pressure can be an important indicator and/or therapeutic intervention for various ocular conditions, such as glaucoma.

SUMMARY

The term embodiment and like terms are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, not this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this disclosure, any or all drawings and each claim.

Embodiments of the present disclosure include a method, comprising: capturing imaging data of a retina of an eye, wherein the imaging data includes first topographical data and second topographical data, wherein the second topographical data is captured subsequent the first topographical data, and wherein the imaging data is associated with an imaged volume of the eye; identifying vasculature using the imaging data, wherein identifying vasculature includes comparing the first topographical data to the second topographical data; generating a connectivity model of vasculature of the retina using the identified vasculature; and calculating deformation data of at least a portion of the imaged volume of the eye, wherein calculating deformation data includes using at least one of the imaging data and additional imaging data associated with the imaged volume of the eye.

In some cases, the method further comprises capturing additional imaging data of the retina of the eye, wherein an intraocular pressure of the eye when capturing the additional imaging data is different than when capturing the imaging data, and wherein calculating deformation data includes using the imaging data and the additional imaging data. In some cases, capturing the imaging data and capturing the additional imaging data occurs in a single session. In some cases, calculating deformation data includes comparing the first topographical data and the second topographical data. In some cases, the method further comprises generating a topographical map of retinal vasculature using the identified vasculature and the imaging data, wherein generating the connectivity model includes using the topographical map of retinal vasculature. In some cases, generating the connectivity model includes using the deformation data. In some cases, calculating the deformation data includes using the connectivity model. In some cases, updating the connectivity model using the deformation data. In some cases, updating the deformation data using the connectivity model. In some cases, the method further comprises generating a deformation map using the deformation data; and colocalizing the connectivity model and the deformation map. In some cases, the method further comprises generating a strain and connectivity model using the colocalized connectivity model and the deformation map. In some cases, the method further comprises predicting retinal blood perfusion using the colocalized connectivity model and the deformation map. In some cases, the method further comprises determining a diagnosis, wherein determining a diagnosis comprises using the colocalized connectivity model and deformation map. In some cases, determining the diagnosis further comprises applying historical data to the colocalized connectivity model and deformation map. In some cases, capturing the imaging data comprises capturing imaging data using an optical coherence tomography system. In some cases, capturing imaging data comprises capturing the first topographical data and the second topographical data in a single session.

Embodiments of the present disclosure include a system, comprising: an optical coherence tomography instrument for capturing imaging data of a retina of an eye; one or more data processors; and a non-transitory computer-readable storage medium containing instructions which, when executed on the one or more data processors, cause the one or more data processors to perform operations including: receiving the imaging data from the optical coherence tomography instrument, wherein the imaging data includes first topographical data and second topographical data, wherein the second topographical data is captured subsequent the first topographical data, and wherein the imaging data is associated with an imaged volume of the eye; identifying vasculature using the imaging data, wherein identifying vasculature includes comparing the first topographical data to the second topographical data; generating a connectivity model of vasculature of the retina using the identified vasculature; and calculating deformation data of at least a portion of the imaged volume of the eye, wherein calculating deformation data includes using at least one of the imaging data and additional imaging data associated with the imaged volume of the eye.

In some cases, the operations further comprise receiving additional imaging data from the optical coherence tomography instrument, wherein an intraocular pressure of the eye associated with the additional imaging data is different from an intraocular pressure of the eye associated with the imaging data, and wherein calculating deformation data includes using the imaging data and the additional imaging data. In some cases, the imaging data is captured during a single session and wherein the additional imaging data is captured during the single session. In some cases, calculating deformation data includes comparing the first topographical data and the second topographical data. In some cases, the operations further comprise generating a topographical map of retinal vasculature using the identified vasculature and the imaging data, wherein generating the connectivity model includes using the topographical map of retinal vasculature. In some cases, generating the connectivity model includes using the deformation data. In some cases, calculating the deformation data includes using the connectivity model. In some cases, the operations further comprise updating the connectivity model using the deformation data. In some cases, the operations further comprise updating the deformation data using the connectivity model. In some cases, the operations further comprise: generating a deformation map using the deformation data; and colocalizing the connectivity model and the deformation map. In some cases, the operations further comprise generating a strain and connectivity model using the colocalized connectivity model and the deformation map. In some cases, the operations further comprise predicting retinal blood perfusion using the colocalized connectivity model and the deformation map. In some cases, the operations further comprise determining a diagnosis, wherein determining a diagnosis comprises using the colocalized connectivity model and deformation map. In some cases, determining the diagnosis further comprises applying historical data to the colocalized connectivity model and deformation map. In some cases, the imaging data is capturing during a single session.

BRIEF DESCRIPTION OF THE DRAWINGS

The specification makes reference to the following appended figures, in which use of like reference numerals in different figures is intended to illustrate like or analogous components.

DETAILED DESCRIPTION

Figure 1:
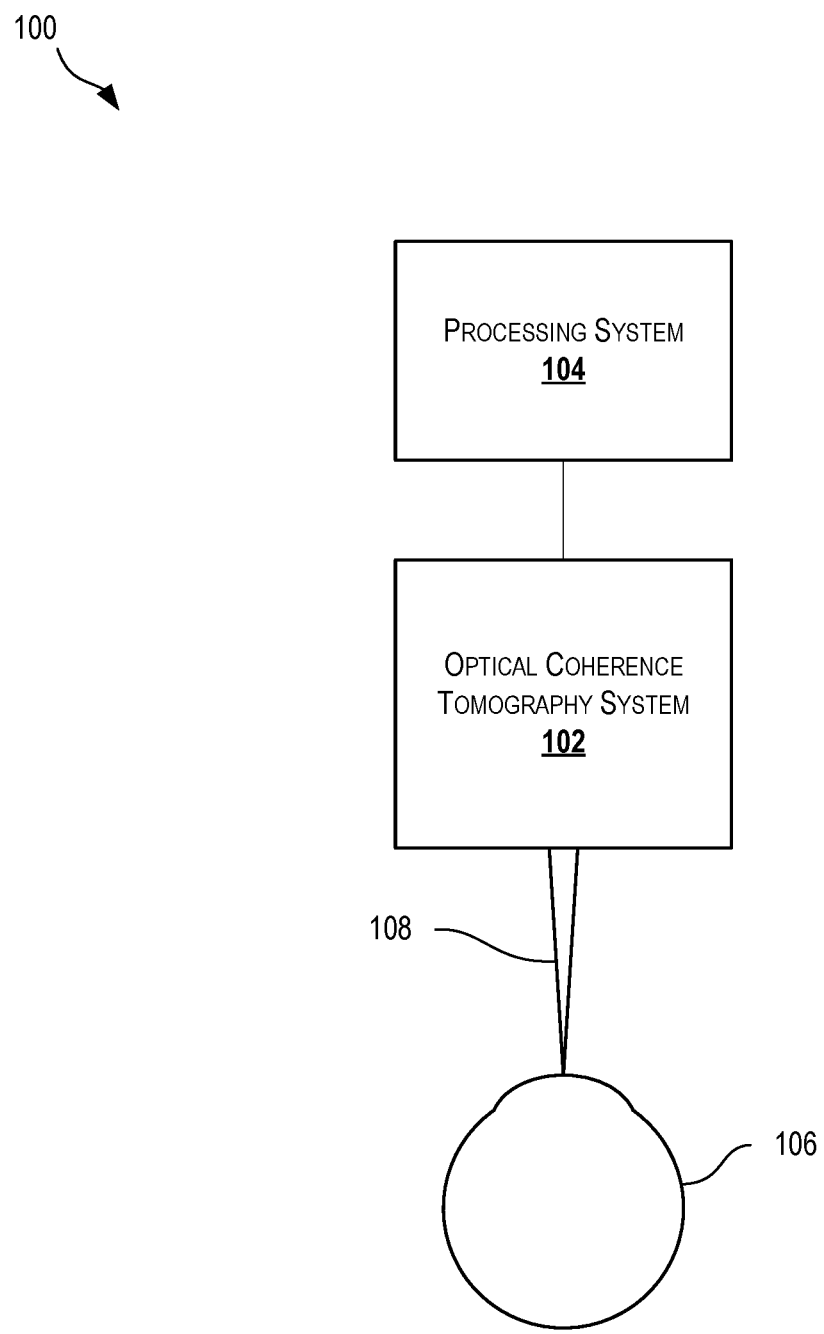
FIG. 1 is a schematic diagram depicting a retinal measurement and analysis system according to certain aspects of the present disclosure.

Certain aspects and features of the present disclosure relate to tools and techniques for quantizing the relationship between morphological changes to an eye due to intraocular pressure changes and blood perfusion changes in the retina. Diagnostic data can be generated by processing colocalized retinal perfusion data and optic nerve head (ONH) mechanical deformation data. Changes in blood retinal perfusion due to changes in intraocular pressure (IOP) can be monitored and quantified and predicted by colocalizing the retinal perfusion data with the ONH mechanical deformation data. Optical coherence tomography-angiography (OCT-A) can be used to generate both retinal perfusion data and mechanical deformation data for an imaged volume. A three-dimensional model (e.g., connectivity map or connectivity model) of the vasculature can be generated from the OCT-A imaging data and used to predict changes in blood perfusion in various areas of the retina due to IOP-induced mechanical deformations. The predicted response in retina blood perfusion due to IOP-induced mechanical deformations can be used as a biomarker and to monitor and predict progression of retina degenerative diseases.

Elevated IOP can be indicative of glaucoma and other ocular conditions. Lowering IOP is the only proven therapeutic intervention for glaucoma. IOP is also related to blood perfusion of the retina. The amount of blood perfusion in the retina is primarily dependent upon the difference between systemic and intraocular pressures. Increases in intraocular pressure without a change to systemic pressure correlates to a decrease in blood perfusion, as well as an alteration of the ocular tissue morphology.

In optical coherence tomography, coherent light is used to capture three-dimensional imaging data through interferometry (e.g., analysis of interference between split coherent light reflected from a sample and a reference mirror). Optical coherence tomography can be used to generate three-dimensional imaging data of an imaged volume. Generally, optical coherence tomography can be used to capture B-scans of a retina, or cross-sectional slice images of a retina. By combining multiple, displaced B-scans, a three-dimensional topographical map of the retina can be generated. The topographical map generated using OCT is limited to displaying information about the shape and structure of the imaged tissue.

Optical coherence tomography angiography (OCT-A) is a form of OCT that expands on the capabilities of OCT. OCT-A involves taking multiple, optionally sequential, measurements of individual volumes (e.g., voxels) of the imaged volume to not only create a topographical map as done in traditional OCT, but to also attempt to identify whether that voxel can be characterized as vasculature or non-vasculature structure. By comparing the measurements taken (e.g., intensity) of a single voxel at different times, a determination can be made. If the measurements of the voxel change over time (e.g., change the same or more than a threshold amount), an inference can be made that the voxel represents vasculature, since the changes are likely due to blood movement. If the measurements of the voxel show little or no change over time (e.g., change less than a threshold amount), an inference can be made that the voxel represents non-vasculature structure (e.g., collagen), since measurements of such structures are not likely to change over time. OCT-A data can represent a collection of binary voxels, with each voxel either having a value of 0 or 1, representing time-invariant voxels (e.g., not vasculature) or time-varying voxels (e.g., vasculature), respectively. This data indicating whether or not each voxel of a volume is vasculature can be referred to as an angiography map.

As described in further detail herein, certain aspects of the present disclosure make use of angiography map(s) to mask data from other sources so that only data associated with vasculature is analyzed. For example, as disclosed herein, deformation information can be collected and analysis can be performed (e.g., mechanical strain analysis) to determine information about the eye, and in some cases an angiography map can be used to mask the deformation information so as to only perform the desired calculations (e.g., mechanical strain) on tissue identified as vasculature.

Certain aspects of the present disclosure expand upon the capabilities of OCT-A. The three-dimensional topographical maps generated by OCT-A are inherently noisy and only provide a topographical view that identifies which regions are vasculature and which are not. Certain aspects of the present disclosure involve computing a connectivity model from the three-dimensional topographical map generated by OCT-A. Computing the connectivity model can include generating a three-dimensional model of the vasculature capable of modeling fluid flow through the vasculature.

In some cases, computing a connectivity model can include performing a skeletonization of the three-dimensional topographical maps, such as using the OCT-A data. In some cases, denoising of the three-dimensional topographical map can be performed prior to skeletonization. The skeletonization can include analyzing regions of the three-dimensional topographical map, including groups of adjacent voxels indicative of vasculature, to generate a "skeleton" associated with the three-dimensional shape of the vasculature of the measured area. Any suitable technique can be used. In some cases, a thinning technique can successively erode away the outermost voxels of a group of adjacent voxels, while simultaneously preserving the end points, to approximate connected segments (e.g., lines or curves), which can correlate with the vasculature. In some cases, a distance transform technique can be used to generate a skeleton correlated with the vasculature. In some cases, a Voronoi-skeleton technique can be used to generate a skeleton correlated with the vasculature.

In some cases, generating the connectivity model can include converting a skeletonization of the three-dimensional topographical maps into a three-dimensional graph representative of the vessel tree of the vasculature. The skeleton generated through skeletonization can include various nodes (e.g., nodal points) indicative of a branching of the vasculature. A three-dimensional graph can be generated using the nodal points and optionally establishing connections between these points. In some cases, conversion to a three-dimensional graph can permit the efficient exploitation of computational algorithms to characterize morphological parameters of the vessel tree of the vasculature. For example, once the nodes of the graph, which correlate to branching points in the vasculature, are identified, it can be easy to compute distance between two nodal points, which can optionally include passing through intermediate nodal points (e.g., the distance between point A and point C may include a the distances between points A and B as well as B and C). The three-dimensional graph can also be used to easily calculate the shortest path from one nodal point to another, which can be useful for blood-flow predictions. Further, the three-dimensional graph can be used to easily determine the number of connections (e.g., branches) across nodal points, which can be used to estimate possible alternative paths for blood flow. Any of these calculations or determinations can be especially useful when combined with deformation information as described herein. While described as a three-dimensional graph, the information can be stored and processed in any suitable manner, which may or may not include a visualization.

In some cases, techniques other than skeletonization can be used to generate a connectivity model.

In some cases, data from an OCT-A system can be collected and used to estimate deformation intensity information (e.g., deformation data) for the retina as the IOP changes over time. Deformation data, which is not normally used by an OCT-A system, can be obtained by measuring the amount of deformation occurring at a voxel and/or a collection of voxels between two different intraocular pressures. For example, in some cases, deformation data is obtained by measuring the deformation of a collection of voxels in a defined region that are identified as vasculature (e.g., based on an angiography map or a connectivity model). The deformation data can be stored in the form of a three-dimensional map, or deformation map (e.g., strain map). The deformation data can be stored as values for a particular change in IOP (e.g., a 10 mmHg change). Deformation data can relate to mechanical strain.

In some cases, computing the connectivity model can include using the deformation map. For example, the deformation map can be used to validate whether a voxel is correctly identified as vasculature or non-vasculature structure. Further, the deformation map can be used to help predict and/or validate fluid connections between identified vasculature.

In some cases, the same raw data from an OCT machine can be stored and/or used to generate both a connectivity model (e.g., three-dimensional vasculature model) and a deformation map (e.g., three-dimensional map of deformation intensity information).

Once the connectivity model and deformation map are generated, they can be colocalized to identify regions of the connectivity model that undergo various amounts of strain during changes in IOP. Thus, for a particular change in IOP, the colocalized connectivity model and deformation map can be used to estimate how blood perfusion in the retina will change with respect to the change in IOP. For example, an increase in IOP (e.g., of 10 mmHg) may result in various amounts of deformation of various blood vessels across the connectivity model, as identifiable by the colocalized deformation map, which can then be used by the connectivity model to predict blood flow or a change in blood flow through the now-deformed vasculature of the connectivity model, and thus predict retinal blood perfusion and/or a change in retinal blood perfusion. Generally, measurements can be taken, models can be generated, and predictions can be made for regions of the retina at or near the optic nerve head, although that need not be the case.

Unlike the topographical maps generated by traditional OCT-A, the connectivity model and deformation map can be used to predict how changes in IOP will affect blood perfusion in the retina.

In some cases, measurement techniques other than OCT can be used as appropriate, such as Doppler interferometry or ultrasonic techniques, as long as a connectivity model can be generated and deformation information be obtained (e.g., a deformation map be generated).

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure. The elements included in the illustrations herein may not be drawn to scale.

FIG. 1 is a schematic diagram depicting a retinal measurement and analysis system 100 according to certain aspects of the present disclosure. The measurement and analysis system 100 can include a processing system 104 coupled to an optical coherence tomography system 102 (e.g., an optical coherence tomography instrument and optionally additional hardware for operating the optical coherence tomography instrument). In some cases, the processing system 104 and optical coherence tomography system 102 can be located in a single housing or located in separate housings, including being located near one another or remotely (e.g., in another city, country, or continent).

The optical coherence tomography system 102 can use coherent light 108 to capture measurements from an eye 106, or more specifically from a retina of an eye 106. The optical coherence tomography system 102 can provide raw or processed data to the processing system 104. Processed data can include raw data that has been filtered, denoised, amplified, or otherwise processed, which can also include generation of topographical maps.

The processing system 104 can use the measurements captured from the optical coherence tomography system 102 to generate a connectivity model and a deformation map for the imaged portion of the eye 106, as disclosed herein. In some cases, the processing system 104 can generate predictions of retinal blood perfusion (e.g., ONH blood perfusion) based on a particular change in IOP.

Figure 2:
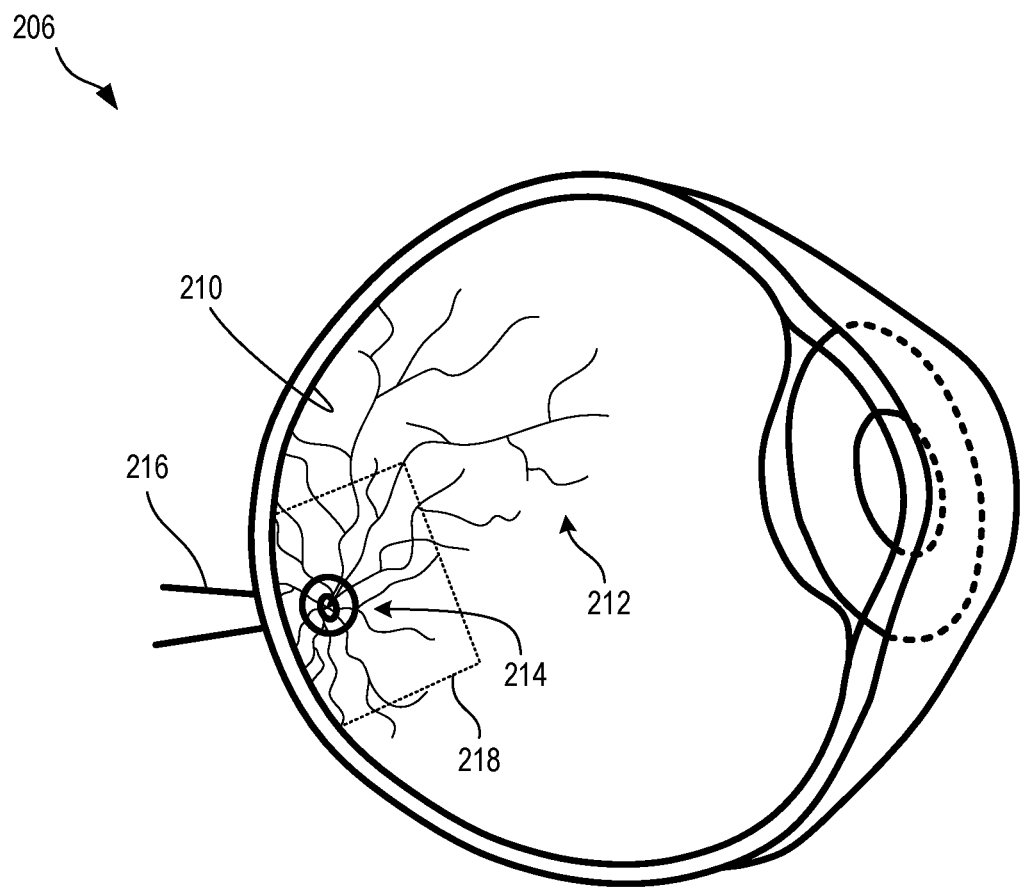
FIG. 2 is a schematic diagram of an eye as measured and modeled according to certain aspects of the present disclosure.

FIG. 2 is a schematic diagram of an eye 206 as measured and modeled according to certain aspects of the present disclosure. The eye 206 can include a retina 210 containing a retinal vasculature 212. The vasculature 212 can contain numerous blood vessels. The retina 210 can include an optic nerve head 214 where the optic nerve 216 couples to the eye 206. During optical coherence tomography or other imaging techniques, an imaged volume 218 is imaged and processed. The vasculature 212 within the imaged volume 218 can be captured, measured, and modeled as described herein. In some cases, the imaged volume 218 can include the optic nerve head 214, however that need not be the case. The imaged volume 218 can take on any suitable shape or size, as available to the measuring instrument (e.g., OCT system).

Figure 3:
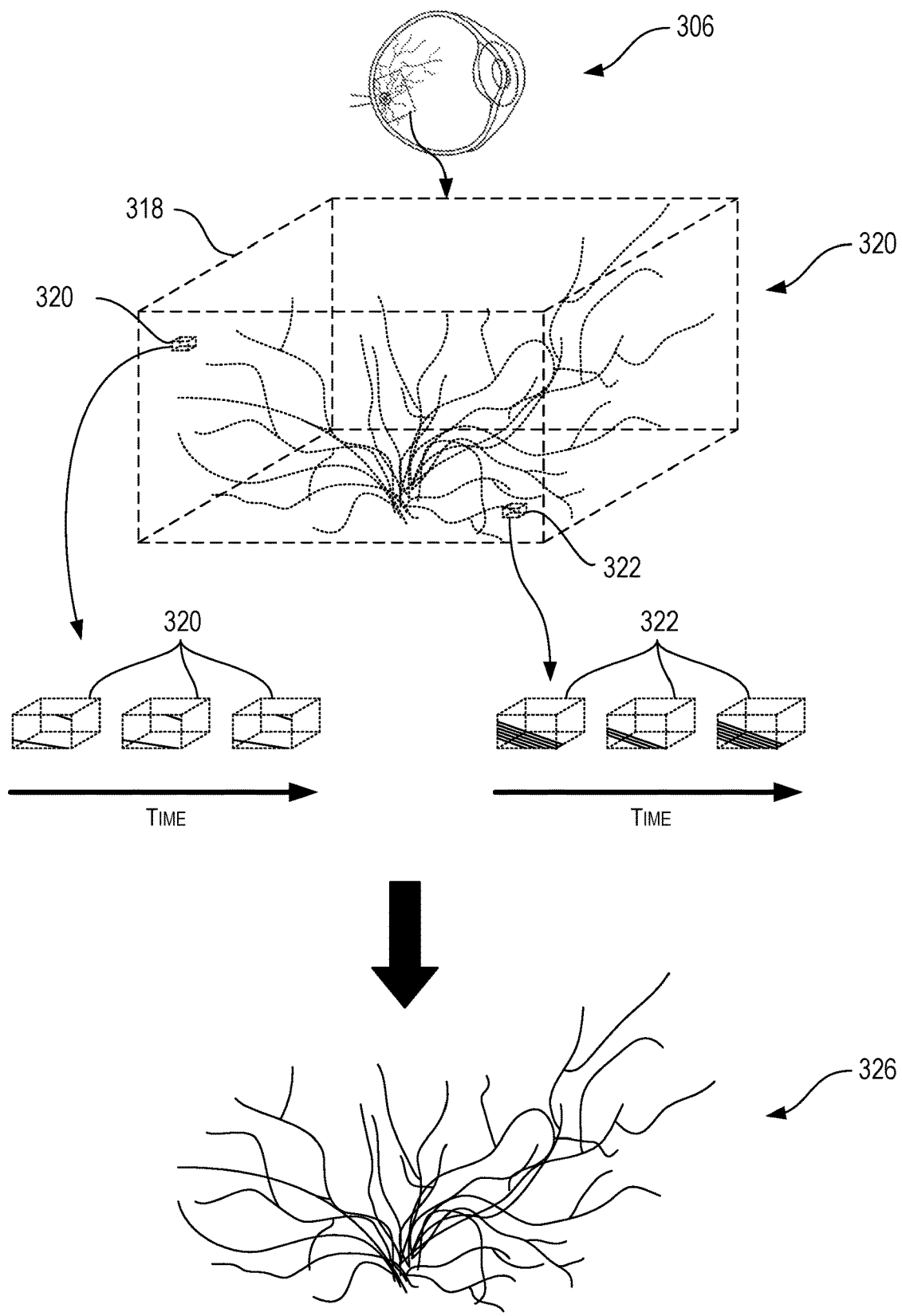
FIG. 3 is a set of schematic diagrams depicting a topographical map of the retina of an eye and a connectivity model generated from the topographical map according to certain aspects of the present disclosure.

FIG. 3 is a set of schematic diagrams depicting a topographical map 320 of the retina of an eye 306 and a connectivity model 326 generated from the topographical map 320 according to certain aspects of the present disclosure. The topographical map 320 can be generated using optical coherence tomography techniques, such as using the optical coherence tomography system 102 of FIG. 1. Eye 306 can be similar to eye 206 of FIG. 2.

The topographical map 320 can be generated for a particular imaged volume 318 by taking measurements of each voxel 320, 322 of the imaged volume 318. As depicted in FIG. 3, the voxels 320, 322 are shown in exaggerated size for illustrative purposes. The topographical map 320 can be simply topographical in nature, or can also include vasculature information. As described herein, by taking multiple measurements of each voxel 320, 322 over time, each voxel 320, 322 can be characterized as being either vasculature or not. As depicted in FIG. 3, voxel 320 is schematically depicted as having constant measurements over time (depicted by constant, diagonal lines), and thus can be characterized as not being vasculature. However, voxel 322 is schematically depicted as having changing measurements over time (depicted by changing diagonal lines), and thus can be characterized as being vasculature.

As described in further detail herein, analysis of the topographical map 320 and vasculature information can be used to generate a connectivity model 326 of the vasculature within the imaged volume 318 of the eye 306. In some cases, multiple topographical maps 320 taken at different intraocular pressures can be compared and used to generate and/or improve the connectivity model 326.

While described with reference to a topographical map 320, the connectivity model 326 can be generated procedurally without generation of an intermediate graphical representation (e.g., visual topographical map) of the imaged volume 318.

Figure 4:
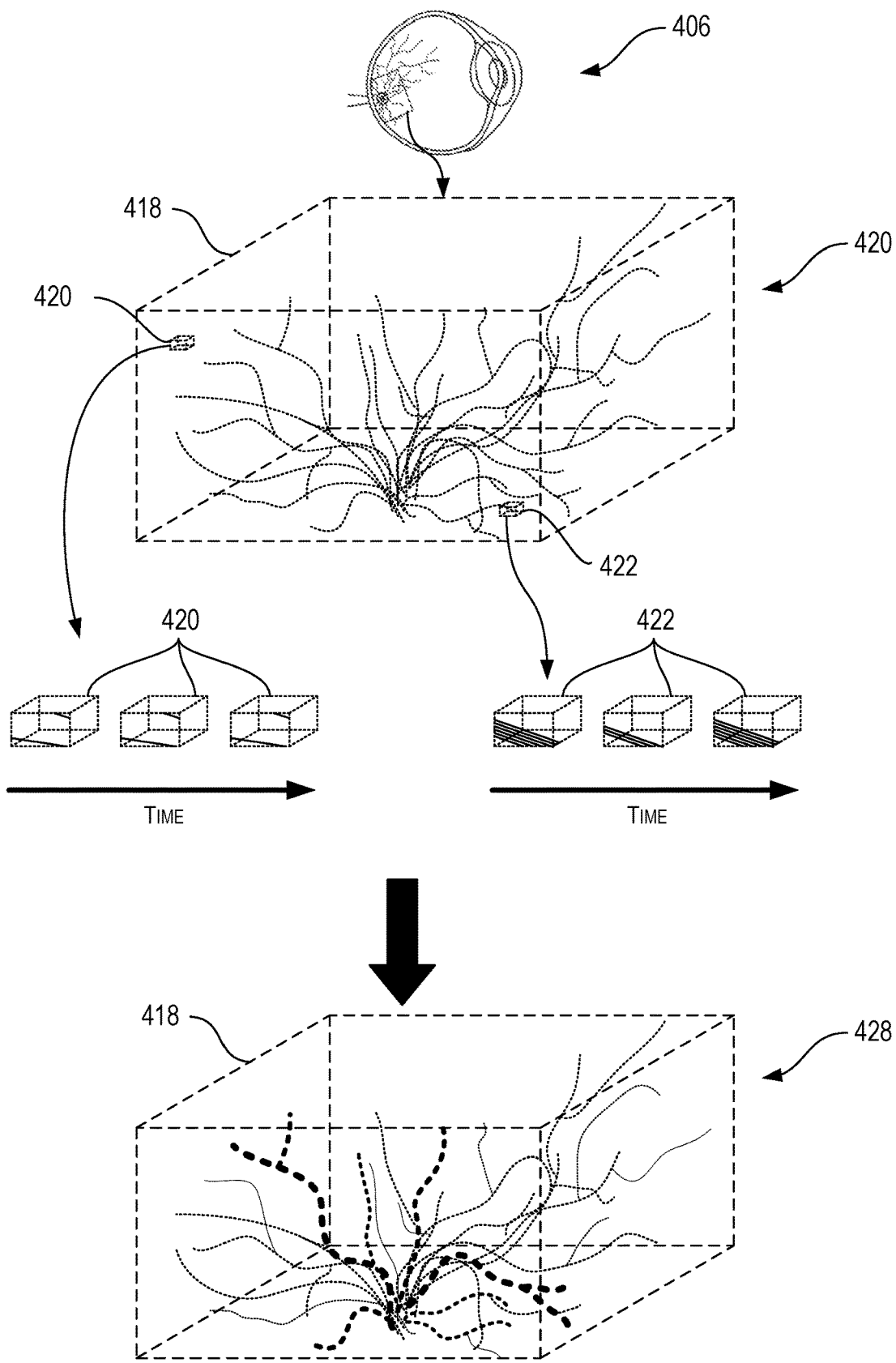
FIG. 4 is a set of schematic diagrams depicting a topographical map of the retina of an eye and a deformation map generated from the topographical map according to certain aspects of the present disclosure.

FIG. 4 is a set of schematic diagrams depicting a topographical map 420 of the retina of an eye 406 and a deformation map 428 generated from the topographical map 420 according to certain aspects of the present disclosure. The topographical map 420 can be generated using optical coherence tomography techniques, such as using the optical coherence tomography system 102 of FIG. 1. Eye 406 can be similar to eye 206 of FIG. 2.

The topographical map 420 can be generated for a particular imaged volume 418 by taking measurements of each voxel 420, 422 of the imaged volume 418. As depicted in FIG. 4, the voxels 420, 422 are shown in exaggerated size for illustrative purposes. The topographical map 420 can be simply topographical in nature, or can also include vasculature information. As described herein, by taking multiple measurements of each voxel 420, 422 over time, each voxel 420, 422 can be characterized as being either vasculature or not. As depicted in FIG. 4, voxel 420 is schematically depicted as having constant measurements over time (depicted by constant, diagonal lines), and thus can be characterized as not being vasculature. However, voxel 422 is schematically depicted as having changing measurements over time (depicted by changing diagonal lines), and thus can be characterized as being vasculature.

As described in further detail herein, analysis of the topographical map 420 and vasculature information changes between at least two different intraocular pressures can be used to generate a deformation map 428 of the vasculature within the imaged volume 418 of the eye 406. By detecting voxels or regions (e.g., collections of adjacent voxels) that are representative of deforming tissue, changes in those voxels or regions due to changes in intraocular pressure can be used to obtain deformation measurements. Collected deformation measurements for a particular imaged volume 418 can be represented as a deformation map 428, whether graphically or numerically. The deformation map 428 is schematically depicted in FIG. 4 to show regions of higher strain with bolder lines and regions of lower strain with thinner lines. While described with reference to a topographical map 420, the deformation map 428 can be generated procedurally without generation of an intermediate graphical representation (e.g., visual topographical map) of the imaged volume 418.

Figure 5:
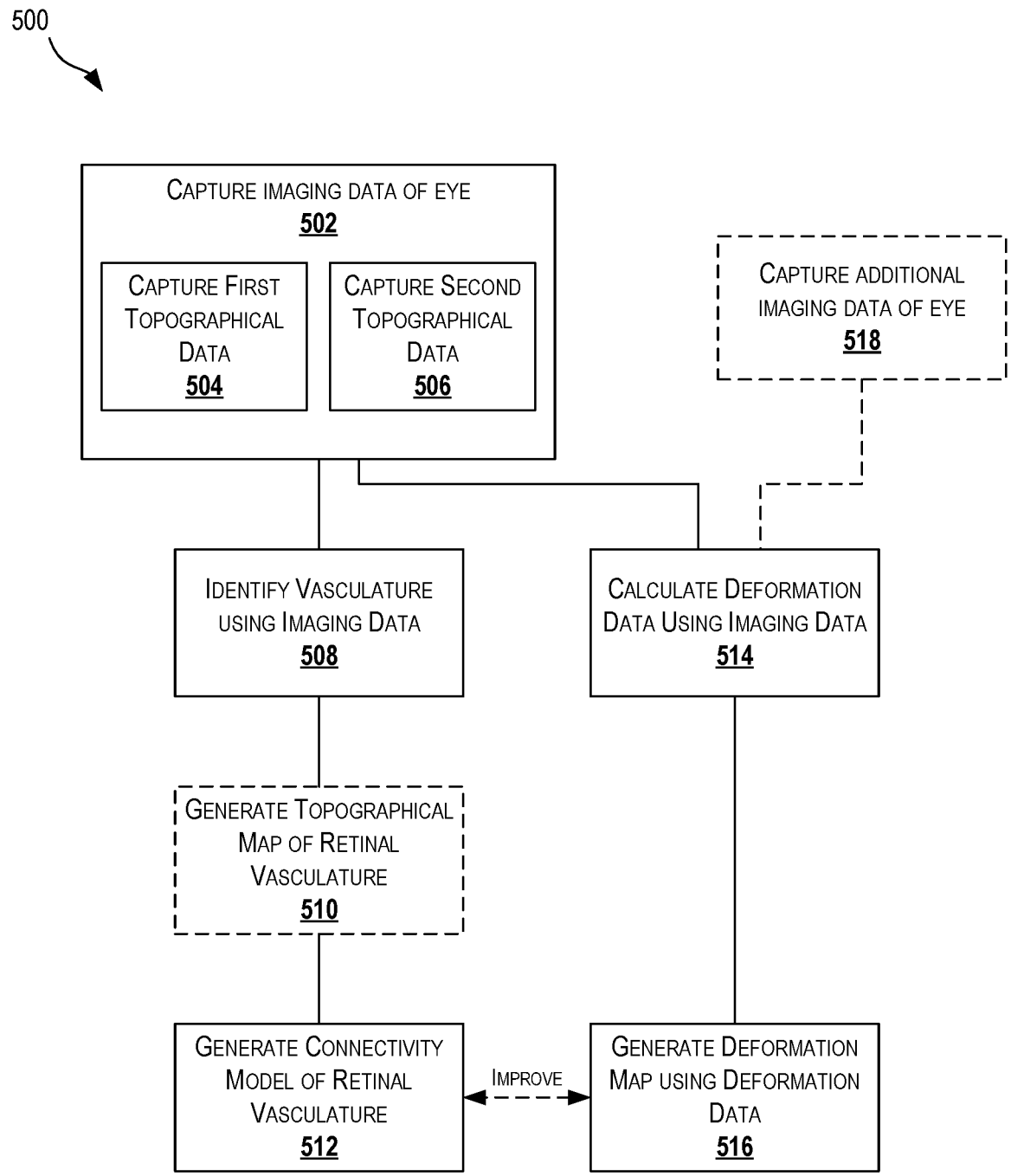
FIG. 5 is a flowchart depicting a process for generating a connectivity model and deformation map for an eye, according to certain aspects of the present disclosure.

FIG. 5 is a flowchart depicting a process 500 for generating a connectivity model and deformation map for an eye, according to certain aspects of the present disclosure. At block 502, imaging data of an eye can be captured. The imaging data can be captured using any suitable technique, such as using an OCT system (e.g., OCT system 102 of FIG. 1).

Capturing imaging data at block 502 can include capturing first topographical data at block 504 and capturing second topographical data at block 506. The first topographical data can include topographical measurement(s) for an imaged volume of the eye. The second topographical data can include topographical measurement(s) for the same imaged volume of the eye, but taken at a different time. In some cases, the second topographical data is taken at a different intraocular pressure than the first topographical data. In some cases, the intraocular pressure at the time each of the first and second topographical data is captured can be stored (e.g., as metadata) along with the imaging data captured at block 502. In some cases, imaging data can include topographical data and/or any other related metadata. Capturing imaging data of the eye at block 502 can include capturing numerous iterations of topographical data (e.g., beyond just first and second topographical data) at numerous different times, all of which can include the imaged volume of the eye. In some cases, capturing imaging data of the eye at block 502, including capturing at least first and second topographical data of the imaged volume at blocks 504 and 506, can be considered a single OCT-A scan.

Capturing first topographical data at block 504 and capturing second topographical data at block 506 can each refer to capture of a single voxel of information, in which case blocks 504 and 506 can be repeated as necessary for each voxel. In such a case, the coherent light of an OCT scanner being used to capture the data may capture first and second topographical data at one or more voxels before being scanned to focus on a different region of the eye, at which point first and second topographical data capture can be repeated for that different region. In some cases, however, capturing first topographical data at block 504 and capturing second topographical data at block 506 can each refer to capturing topographical data of an entire imaged volume. In such a case, the coherent light of an OCT scanner being used to capture the data may scan over the eye to capture the entire imaged volume and store the data as the first topographical data before repeating the process at a later time to capture and store the second topographical data.

In some cases, capturing first topographical data at block 504 and capturing second topographical data at block 506 can occur in a single session or in a single scan. A single session or a single scan can each include measurements taken within a period of time spanning no more than 1 millisecond, 3 milliseconds, 5 milliseconds, 7 milliseconds, 10 milliseconds, tens of milliseconds, 100 milliseconds, hundreds of milliseconds, 1 second, 3 seconds, 5 seconds, 7 seconds, 10 seconds, tens of seconds, hundreds of seconds, 1 minute, 2 minutes, 3 minutes, 4 minutes, 5 minutes, 6 minutes, 7 minutes, 8 minutes, 9 minutes, or 10 minutes, although in some cases a single session or scan may take longer. For example, first and second topographical data can be captured within 10 milliseconds of one another. In some cases, a single session can include one scan or multiple scans. In some cases, a single session can include measurements taken between the time a patient's eye is positioned to be measured by the measurement device (e.g., OCT system) and the time the patient's eye is removed from that position. For example, a patient's head may be placed on a rest or guide such that the patient's eye is in position to be measured by an OCT system, in which case the single session may begin when the patient's head is placed on the rest or guide and may end when the patient's head is next removed from the rest or guide. In such cases, multiple OCT or OCT-A scans may occur in the single session. In some cases, first and second topographical data may be captured across multiple sessions. As used herein, historical data can refer to data collected and/or generated at a time prior to the current session (e.g., data from a prior session).

At block 508, vasculature is identified using the imaging data. As described herein, comparison of topographical data (e.g., intensity measurements) between two or more time periods can be used to identify if a particular voxel is or is not vasculature. At optional block 510, a topographical map of the retinal vasculature can be generated. Generation of the topographical map of the retinal vasculature can include generating a three-dimensional topographical map based on the imaging data and can include an indication of regions (e.g., collections of voxels) that have been identified as vasculature at block 508. In some cases, it can be preferable to identify vasculature at block 508 using imaging data captured (e.g., at block 502) at relatively low intraocular pressures, since more of the vasculature would likely be represented in the topographical data and not potentially obscured by deformations associated with higher pressures.

At block 512, a connectivity model of the retinal vasculature can be generated. Generating the connectivity model can include using the imaging data, including the voxels or other regions identified as vasculature at block 508. In some cases, generating the connectivity model can include using the topographical map of the retinal vasculature generated at block 510. The connectivity model can be generated to establish a three-dimensional, connected vasculature. Generating the connectivity model at block 512 can be generating the connectivity model using data from an OCT-A scan, as described herein.

In some cases, an existing connectivity model can be improved at block 512 via further iterations of block 502, block 508, and optionally block 510. For example, an existing connectivity model for a particular eye may be improved upon by capturing additional imaging data of the eye in an additional iteration of block 502, which may include re-using the first or second topographical data as the first topographical data in the additional iteration of block 502, or may include capturing all new topographical data; identifying vasculature using that additional imaging data at block 508; optionally generating a topographical map of the retinal vasculature based on that additional imaging data at block 510; and updating the existing connectivity model of the retinal vasculature at bock 512.

At block 514, deformation data is calculated using imaging data. Deformation data can include information and/or representations of how the topography of the imaged volume changes with respect to a variable, such as intraocular pressure. Calculating deformation data at block 514 can include receiving imaging data including first and second topographical data (e.g., first and second topographical measurements) and variable data related to the first and second topographical data (e.g., intraocular pressure data for the first topographical measurement(s) and intraocular pressure data for the second topographical measurement(s), or merely an amount of change of intraocular pressure data between the first and second topographical measurements). The imaging data and variable data can be collected during a single OCT-A scan. However, in some cases, calculating deformation data at block 514 can include comparing imaging data collected at block 502 (e.g., first and/or second topographical data) with additional imaging data collected at optional block 518 (e.g., additional topographical data), which can include comparing variable information for the image data and additional image data, such as intraocular pressure and additional intraocular pressure, respectively. As used with respect to blocks 518 and 514, the term "additional" can refer to prior or subsequent, such as prior imaging data or subsequent imaging data. In some cases, capturing additional imaging data at block 518 can include capturing additional imaging data during an OCT or OCT-A scan performed subsequent to the OCT-A scan performed at block 502. In some cases, capturing the additional imaging data at block 518 can include capturing the additional imaging data of the imaged volume of the eye at a higher intraocular pressure than the imaging data captured at block

502. However, in some cases, the intraocular pressure when the additional imaging data is captured at block 518 is lower than when the imaging data is captured at block 502. Calculating deformation data at block 514 can be performed on a voxel-by-voxel basis, on a regional basis, or for an entire imaged volume.

In some cases, deformation data can be calculated at block 514 using additional imaging data captured at block 518 and without using the imaging data captured at block 502. For example, the connectivity model can be generated using a first OCT-A scan and the deformation data can be calculated using a second OCT or OCT-A scan and optionally additional OCT or OCT-A scans. In such cases, the imaged volume associated with the imaging data captured at block 502 can overlap with the imaged volume associated with the additional imaging data captured at block 518. The overlapping region can be used for colocalization, as described herein.

At block 516, a deformation map can be generated using the deformation data. The deformation map can be a model, dataset, and/or three-dimensional representation of the calculated strain of the topography of the imaged volume. In some cases, calculation of deformation data and/or generation of the deformation map can be constrained to only those regions identified as vasculature at block 508. While described as a deformation map, in some cases, the deformation map can include any suitable deformation-related information, such as stress or force, strain, or temperature.

In some cases, the deformation map can be used to improve the connectivity model of the retinal vasculature. For example, if the deformation map shows regions of deformations that are characteristic of being or not being vasculature, and if the connectivity model shows that region as being opposite of what the deformation map is indicating, the connectivity model may be updated accordingly. In some cases, initial generation of the connectivity model at block 512 can include using a generated deformation map as well as any vasculature information and/or topographical map data. Likewise, in some cases, the deformation map can be improved and/or initially generated using the connectivity model. For example, calculation of deformation data at block 514 and/or generation of the deformation map at block 516 may be constrained to only those regions of the imaged volume that are vasculature in the connectivity model.

Figure 6:
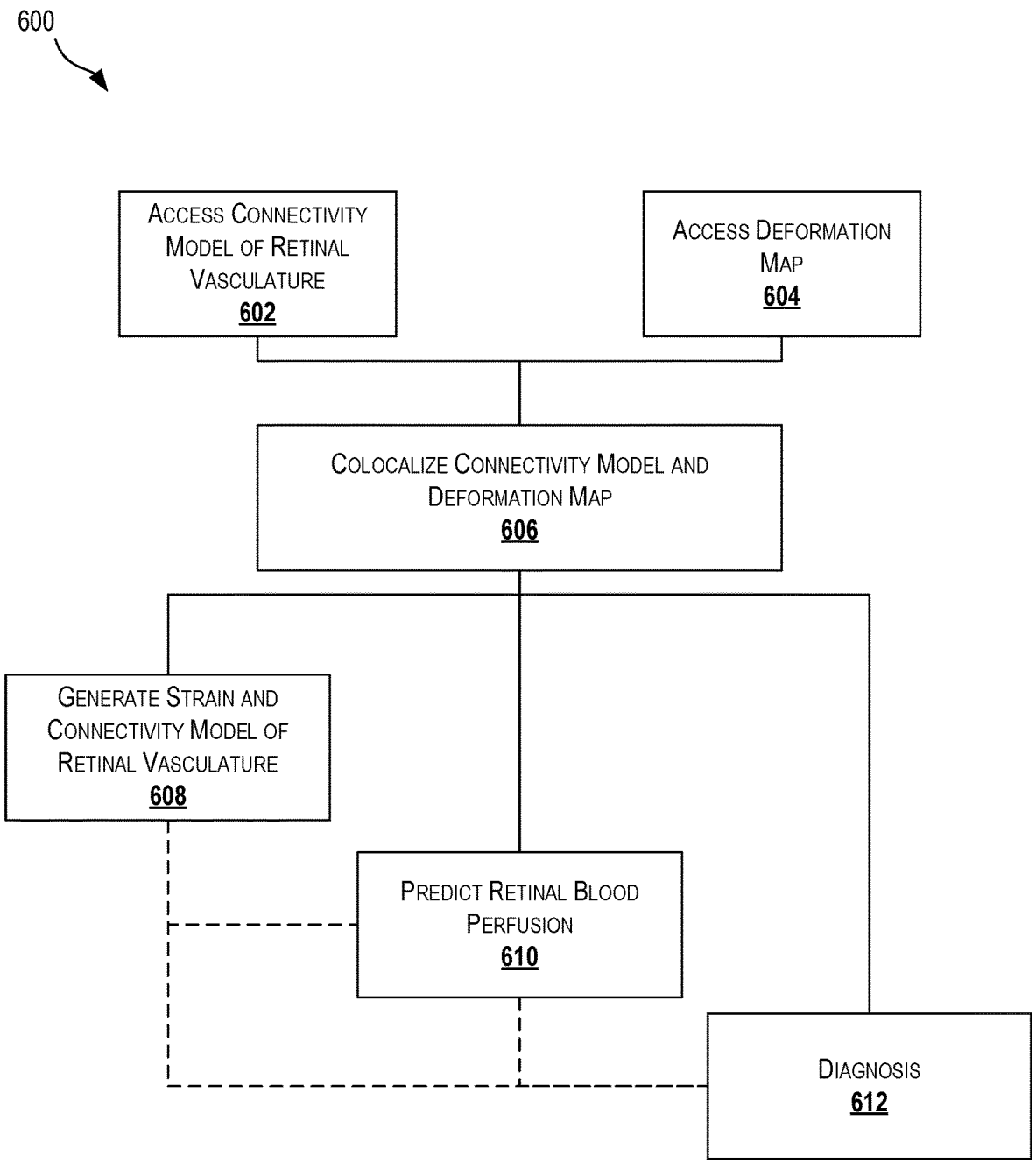
FIG. 6 is a flowchart depicting a process for using a connectivity model and deformation map according to certain aspects of the present disclosure.

FIG. 6 is a flowchart depicting a process 600 for using a connectivity model and deformation map according to certain aspects of the present disclosure. At block 602, a connectivity model of retinal vasculature for an eye is accessed. Accessing the connectivity model can include accessing a stored model or generating a model, such as described with reference to FIG. 5. At block 604, a deformation map for the eye is accessed. Accessing the deformation map can include accessing a stored deformation map or generating a deformation map, such as described with reference to FIG. 5.

At block 606, the connectivity model and deformation map are colocalized. Colocalization can include aligning the connectivity model and the deformation map. Colocalization can include applying deformation data from the deformation map to the connectivity model. As a result of colocalization, changes in certain variables, such as intraocular pressure, can be accurately modeled based not only on the connectivity model, but also on the deformation data for the blood vessels modeled in the connectivity model.

At optional block 608, a strain and connectivity model of the retinal vasculature can be generated using the connectivity model and the deformation map (e.g., via colocalization of the connectivity model and deformation map at block 606). The strain and connectivity model can be a three-dimensional model that models not only the connectivity between blood vessels in the imaged volume, but also models the structural characteristics (e.g., strain, stress/strain relationships, deformations, or other characteristics of the deformation map) for the modeled blood vessels.

At optional block 610, retinal blood perfusion can be predicted. Predicting retinal blood perfusion can include using the colocalized connectivity model and deformation map from block 606 or using the generated strain and connectivity model of block 608. Predicting retinal blood perfusion can include predicting the blood perfusion for a particular region of the imaged volume and/or predicting blood perfusion for more than the imaged volume, using the imaged volume as an indicator or guide for predicting non-imaged regions. Predicting retinal blood perfusion can include supplying different conditions to the model(s) (e.g., changes in intraocular pressure, changes in systemic pressure, changes in heart rate, or other changes), to predict how the blood vessels would react to the different conditions and to estimate a quantification of retinal blood perfusion given the supplied conditions.

At optional block 612, a diagnosis can be made. Making the diagnosis can include using the colocalized connectivity model and deformation map from block 606, using the generated strain and connectivity model of block 608, and/or using the predicted retinal blood perfusion of block 610. Making the diagnosis can include either predicting future behavior of the retinal vasculature (e.g., future blood perfusion or other behavior) using the model(s) or validating current behavior using historical data. For example, with respect to predicting future behavior, current imaging data can be used to generate the connectivity model and deformation map, which can be used as described with respect to FIG. 6 to predict various conditions, such as decreased retinal blood perfusion, under expected future circumstances. Based on the predicted condition (e.g., decreased retinal blood perfusion), a diagnosis may be made. As an example with respect to validating current behavior using historical data, historical data (e.g., from a previous doctor visit), can be used to generate the connectivity model and deformation map. During a current visit, certain conditions can be determined (e.g., current systemic pressure, current intraocular pressure, current heart rate, or other conditions) and applied to the model(s) to achieve expected results. The expected results can be compared to current measurements (e.g., current blood perfusion, current imaging data, model(s) generated using current imaging data, and/or deformation maps generated using current imaging data) to determine if the current results are unexpected or indicative of a diagnosable condition.

Figure 7:
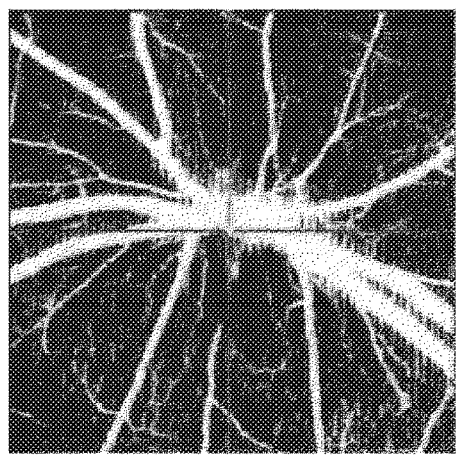
FIG. 7 is a set of two-dimensional images representing data obtained or generated according to certain aspects of the present disclosure.
Figure 7:
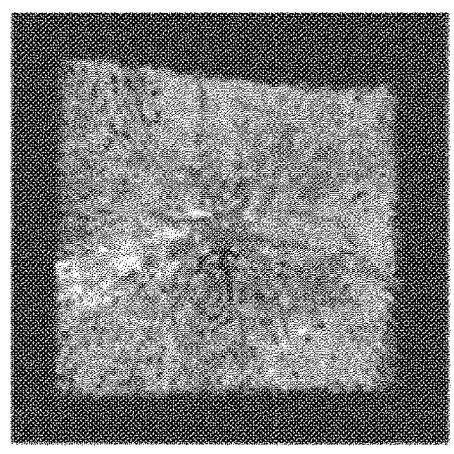
Figure 7:
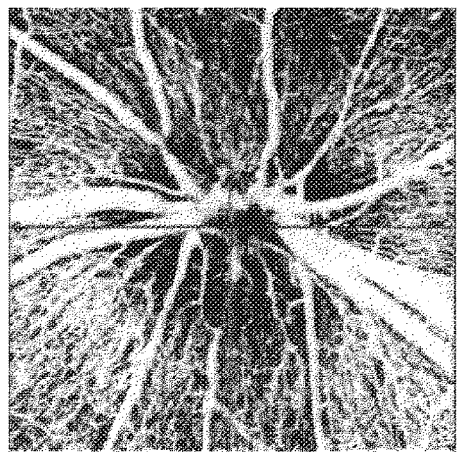
Figure 7:
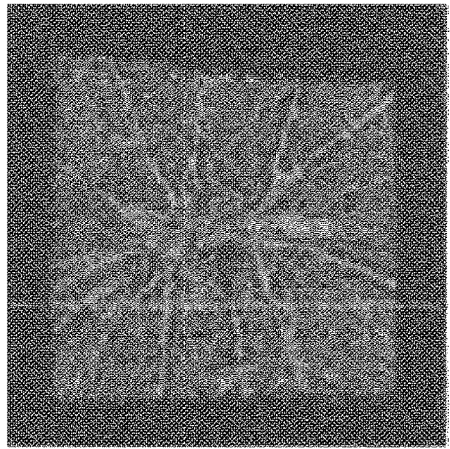
Figure 7:
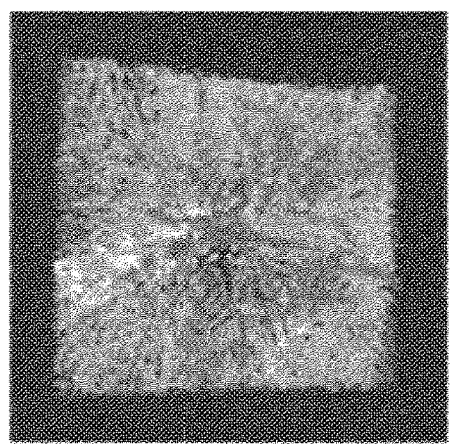

FIG. 7 is a set of two-dimensional images representing data obtained or generated according to certain aspects of the present disclosure. The images depicted in FIG. 7 are two-dimensional, although the data used to generate the images may include three-dimensional data. Two-dimensional images can be generated from the three-dimensional data by viewing a slice of the three-dimensional data or viewing a surface of the three-dimensional data. The images 702, 704, 706, 708, 710 depict different representations of the same region of a retina, specifically a region near the optic nerve head.

Image 702 is a topographical map of the vasculature of a retina around an optic nerve head taken at an intraocular pressure of 10 mmHg. The regions of the image in white have been identified as vasculature, whereas regions in black have been identified as non-vasculature structure. Image 706 is a topographical map of the vasculature of a retina around an optic nerve head taken at an intraocular pressure of 20 mmHg. The regions of the image in white have been identified as vasculature, whereas regions in black have been identified as non-vasculature structure.

Images 704 and 708 are deformation maps of the retina around the optic nerve head generated based on the data from images 702 and 706. The deformation maps of images 704 and 708 depict deformation data for a change in intraocular pressure of 10 mmHg. Lighter regions (e.g., including an area extending towards approximately 11 o'clock from near the center of the optic nerve head, as well as a region towards the bottom-left of the image) are representative of higher strain, whereas darker regions are representative of lower strain.

Image 710 is a two-dimensional representation of a connectivity model of the vasculature of the retina around the optic nerve head. The connectivity model can be generated using data related to one or more of images 702, 704, and 706. As described with reference to FIG. 6, colocalization of the connectivity model and the deformation map can be visualized by comparing the same regions of images 708 and 710. For example the region of the connectivity model that is also indicated as having higher strain in image 708 may deform more under high intraocular pressure, and therefore perfusion around that area when intraocular pressure increase may decrease. The connectivity model can facilitate determining how deformations in those vessels may affect other, connected vessels.

Individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination can correspond to a return of the function to the calling function or the main function. Various processes described herein, such as those described with respect to FIGS. 5 and 6, may be stored as instructions on a non-transitory machine-readable storage medium for operation by a computing device, such as processing system 104 of FIG. 1. Further, any models or other data, such as those generated with respect to FIGS. 5 and 6, may be stored on a non-transitory machine-readable storage medium.

The term "machine-readable storage medium" or "computer-readable storage medium" includes, but is not limited to, portable or non-portable storage devices, optical storage devices, and various other mediums capable of storing, containing, or carrying instruction(s) and/or data. A machine-readable medium may include a non-transitory medium in which data can be stored and that does not include carrier waves and/or transitory electronic signals propagating wirelessly or over wired connections. Examples of a non-transitory medium may include, but are not limited to, a magnetic disk or tape, optical storage media such as compact disk (CD) or digital versatile disk (DVD), flash memory, memory or memory devices. A computer-program product may include code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

In the foregoing description, for the purposes of illustration, methods were described in a particular order. It should be appreciated that in alternate embodiments, the methods may be performed in a different order than that described. It should also be appreciated that the methods described above may be performed by hardware components or may be embodied in sequences of machine-executable instructions, which may be used to cause a machine, such as a general-purpose or special-purpose processor or logic circuits programmed with the instructions to perform the methods. These machine-executable instructions may be stored on one or more machine readable mediums, such as CD-ROMs or other type of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software.

Where components are described as being configured to perform certain operations, such configuration can be accomplished, for example, by designing electronic circuits or other hardware to perform the operation, by programming programmable electronic circuits (e.g., microprocessors, or other suitable electronic circuits) to perform the operation, or any combination thereof.

Furthermore, embodiments may be implemented by hardware, software, firmware, middleware, microcode, hardware description languages, or any combination thereof. When implemented in software, firmware, middleware or microcode, the program code or code segments to perform the necessary tasks (e.g., a computer-program product) may be stored in a machine-readable medium. A processor(s) may perform the necessary tasks.

Systems depicted in some of the figures may be provided in various configurations. In some embodiments, the systems may be configured as a distributed system where one or more components of the system are distributed across one or more networks in a cloud computing system.

The foregoing description of the embodiments, including illustrated embodiments, has been presented only for the purpose of illustration and description and is not intended to be exhaustive or limiting to the precise forms disclosed. Numerous modifications, adaptations, and uses thereof will be apparent to those skilled in the art.

As used below, any reference to a series of examples is to be understood as a reference to each of those examples disjunctively (e.g., "Examples 1-4" is to be understood as "Examples 1, 2, 3, or 4").

Example 1 is a method, comprising: capturing imaging data of a retina of an eye, wherein the imaging data includes first topographical data and second topographical data, wherein the second topographical data is captured subsequent the first topographical data, and wherein the imaging data is associated with an imaged volume of the eye; identifying vasculature using the imaging data, wherein identifying vasculature includes comparing the first topographical data to the second topographical data; generating a connectivity model of vasculature of the retina using the identified vasculature; and calculating deformation data of at least a portion of the imaged volume of the eye, wherein calculating deformation data includes using at least one of the imaging data and additional imaging data associated with the imaged volume of the eye.

Example 2 is the method of example(s) 1, further comprising capturing additional imaging data of the retina of the eye, wherein an intraocular pressure of the eye when capturing the additional imaging data is different than when capturing the imaging data, and wherein calculating deformation data includes using the imaging data and the additional imaging data.

Example 3 is the method of example(s) 2, wherein capturing the imaging data and capturing the additional imaging data occurs in a single session.

Example 4 is the method of example(s) 1-3, wherein calculating deformation data includes comparing the first topographical data and the second topographical data.

Example 5 is the method of example(s) 1-4, further comprising generating a topographical map of retinal vasculature using the identified vasculature and the imaging data, wherein generating the connectivity model includes using the topographical map of retinal vasculature.

Example 6 is the method of example(s) 1-5, wherein generating the connectivity model includes using the deformation data.

Example 7 is the method of example(s) 1-5, wherein calculating the deformation data includes using the connectivity model.

Example 8 is the method of example(s) 1-5, further comprising updating the connectivity model using the deformation data.

Example 9 is the method of example(s) 1-5, further comprising updating the deformation data using the connectivity model.

Example 10 is the method of example(s) 1-9, further comprising: generating a deformation map using the deformation data; and colocalizing the connectivity model and the deformation map.

Example 11 is the method of example(s) 10, further comprising generating a strain and connectivity model using the colocalized connectivity model and the deformation map.

Example 12 is the method of example(s) 10 or 11, further comprising predicting retinal blood perfusion using the colocalized connectivity model and the deformation map.

Example 13 is the method of example(s) 10-12, further comprising determining a diagnosis, wherein determining a diagnosis comprises using the colocalized connectivity model and deformation map.

Example 14 is the method of example(s) 13, wherein determining the diagnosis further comprises applying historical data to the colocalized connectivity model and deformation map.

Example 15 is the method of example(s) 1-14, wherein capturing the imaging data comprises capturing imaging data using an optical coherence tomography system.

Example 16 is the method of example(s) 1-15, wherein capturing imaging data comprises capturing the first topographical data and the second topographical data in a single session.

Example 17 is a system, comprising: an optical coherence tomography instrument for capturing imaging data of a retina of an eye; one or more data processors; and a non-transitory computer-readable storage medium containing instructions which, when executed on the one or more data processors, cause the one or more data processors to perform operations including: receiving the imaging data from the optical coherence tomography instrument, wherein the imaging data includes first topographical data and second topographical data, wherein the second topographical data is captured subsequent the first topographical data, and wherein the imaging data is associated with an imaged volume of the eye; identifying vasculature using the imaging data, wherein identifying vasculature includes comparing the first topographical data to the second topographical data; generating a connectivity model of vasculature of the retina using the identified vasculature; and calculating deformation data of at least a portion of the imaged volume of the eye, wherein calculating deformation data includes using at least one of the imaging data and additional imaging data associated with the imaged volume of the eye.

Example 18 is the system of example(s) 17, wherein the operations further comprise receiving additional imaging data from the optical coherence tomography instrument, wherein an intraocular pressure of the eye associated with the additional imaging data is different from an intraocular pressure of the eye associated with the imaging data, and wherein calculating deformation data includes using the imaging data and the additional imaging data.

Example 19 is the system of example(s) 18, wherein the imaging data is captured during a single session and wherein the additional imaging data is captured during the single session.

Example 20 is the system of example(s) 17-19, wherein calculating deformation data includes comparing the first topographical data and the second topographical data.

Example 21 is the system of example(s) 17-20, wherein the operations further comprise generating a topographical map of retinal vasculature using the identified vasculature and the imaging data, wherein generating the connectivity model includes using the topographical map of retinal vasculature.

Example 22 is the system of example(s) 17-21, wherein generating the connectivity model includes using the deformation data.

Example 23 is the system of example(s) 17-21, wherein calculating the deformation data includes using the connectivity model.

Example 24 is the system of example(s) 17-21, wherein the operations further comprise updating the connectivity model using the deformation data.

Example 25 is the system of example(s) 17-21, wherein the operations further comprise updating the deformation data using the connectivity model.

Example 26 is the system of example(s) 17-25, wherein the operations further comprise: generating a deformation map using the deformation data; and colocalizing the connectivity model and the deformation map.

Example 27 is the system of example(s) 26, wherein the operations further comprise generating a strain and connectivity model using the colocalized connectivity model and the deformation map.

Example 28 is the system of example(s) 26 or 27, wherein the operations further comprise predicting retinal blood perfusion using the colocalized connectivity model and the deformation map.

Example 29 is the system of example(s) 26-28, wherein the operations further comprise determining a diagnosis, wherein determining a diagnosis comprises using the colocalized connectivity model and deformation map.

Example 30 is the system of example(s) 29, wherein determining the diagnosis further comprises applying historical data to the colocalized connectivity model and deformation map.

Example 31 is the system of example(s) 17-30, wherein the imaging data is capturing during a single session.

The invention claimed is:

1. A method, comprising:

capturing, using an optical coherence tomography instrument, imaging data of a retina of an eye, wherein the imaging data includes first topographical data and second topographical data, wherein the second topographical data is captured subsequent the first topographical data, wherein the imaging data is associated with an imaged volume of the eye, wherein the first topographical data is captured at a first intraocular pressure and the second topographical data is captured at a second intraocular pressure or the imaging data is captured at the first intraocular pressure and additional imaging data associated with the imaged volume of the eye is captured at a second intraocular pressure, wherein the first intraocular pressure is different from the second intraocular pressure, and wherein the imaging data further includes first intraocular pressure data related to the first intraocular pressure and second intraocular pressure data related to the second intraocular pressure or the imaging data further includes first intraocular pressure data related to the first intraocular pressure and the additional imaging data includes second intraocular pressure data related to the second intraocular pressure;

identifying, using a processing system of or in data communication with the optical coherence tomography instrument, vasculature using the imaging data, wherein identifying vasculature includes comparing the first topographical data to the second topographical data to identify voxels in the imaging data that change over time;

generating a connectivity model of vasculature of the retina using the identified vasculature, wherein the connectivity model of vasculature corresponds to a three-dimensional graph representative of a vessel tree of the vasculature;

calculating deformation data for at least a portion of the imaged volume of the eye based on the first intraocular pressure data and the second intraocular pressure data;

generating a deformation map using the deformation data, wherein the deformation map is a data structure corresponding to a three-dimensional map of deformation intensity, and wherein the deformation map describes amounts of strain occurring at one or more voxels between the first intraocular pressure and the second intraocular pressure;

colocalizing the connectivity model and the deformation map to generate a colocalized connectivity model and deformation map identifying regions of the connectivity model that undergo various amounts of strain during changes in the intraocular pressure; and predicting retinal blood perfusion using the colocalized connectivity model and deformation map, wherein the predicting comprises supplying different conditions including changes in intraocular pressure and changes in systemic pressure to the colocalized connectivity model and deformation map to predict how the vasculature would react to the different conditions and estimate a quantification of the retinal blood perfusion given the different conditions.

2. The method of claim 1, further comprising generating a topographical map of retinal vasculature using the identified vasculature and the imaging data, wherein generating the connectivity model includes using the topographical map of retinal vasculature.

3. The method of claim 1, wherein generating the connectivity model includes using the deformation data, or wherein calculating the deformation data includes using the connectivity model.

4. The method of claim 1, further comprising updating the connectivity model using the deformation data, or further comprising updating the deformation data using the connectivity model.

5. The method of claim 1, wherein the first and second intraocular pressure correspond to a fluid pressure in an aqueous humor of the eye.

6. The method of claim 1, further comprising generating a strain and connectivity model using the colocalized connectivity model and deformation map.

7. The method of claim 6, wherein the retinal blood perfusion is predicted using the colocalized connectivity model and deformation map or the strain and connectivity model.

8. The method of claim 7, further comprising determining a diagnosis, wherein determining a diagnosis comprises using the colocalized connectivity model and deformation map or the strain and connectivity model.

9. The method of claim 8, wherein determining the diagnosis further comprises applying historical data to the colocalized connectivity model and deformation map or the strain and connectivity model.

10. A system, comprising:

an optical coherence tomography instrument for capturing imaging data of a retina of an eye;

one or more data processors; and a non-transitory computer-readable storage medium containing instructions which, when executed on the one or more data processors, cause the one or more data processors to perform operations including:

capturing the imaging data using the optical coherence tomography instrument, wherein the imaging data includes first topographical data and second topographical data, wherein the second topographical data is captured subsequent the first topographical data, and wherein the imaging data is associated with an imaged volume of the eye, wherein the first topographical data is captured at a first intraocular pressure and the second topographical data is captured at a second intraocular pressure or the imaging data is captured at the first intraocular pressure and additional imaging data associated with the imaged volume of the eye is captured at a second intraocular pressure, wherein the first intraocular pressure is different from the second intraocular pressure, and wherein the imaging data further includes first intraocular pressure data related to the first intraocular pressure and second intraocular pressure data related to the second intraocular pressure or the imaging data further includes first intraocular pressure data related to the first intraocular pressure and the additional imaging data includes second intraocular pressure data related to the second intraocular pressure;

identifying vasculature using the imaging data, wherein identifying vasculature includes comparing the first topographical data to the second topographical data to identify voxels in the imaging data that change over time;

generating a connectivity model of vasculature of the retina using the identified vasculature, wherein the connectivity model of vasculature corresponds to a three-dimensional graph representative of a vessel tree of the vasculature;

calculating deformation data for at least a portion of the imaged volume of the eye based on the first intraocular pressure data and the second intraocular pressure data;

generating a deformation map using the deformation data, wherein the deformation map is a data structure corresponding to a three-dimensional map of deformation intensity, and wherein the deformation map describes amounts of strain occurring at one or more voxels between the first intraocular pressure and the second intraocular pressure;

colocalizing the connectivity model and the deformation map to generate a colocalized connectivity model and deformation map identifying regions of the connectivity model that undergo various amounts of strain during changes in the intraocular pressure; and predicting retinal blood perfusion using the colocalized connectivity model and deformation map, wherein the predicting comprises supplying different conditions including changes in intraocular pressure and changes in systemic pressure to the colocalized connectivity model and deformation map to predict how the vasculature would react to the different conditions and estimate a quantification of the retinal blood perfusion given the different conditions.

11. The system of claim 10, wherein the operations further comprise generating a topographical map of retinal vasculature using the identified vasculature and the imaging data, wherein generating the connectivity model includes using the topographical map of retinal vasculature.

12. The system of claim 10, wherein generating the connectivity model includes using the deformation data or wherein calculating the deformation data includes using the connectivity model.

13. The system of claim 10, wherein the operations further comprise updating the connectivity model using the deformation data or wherein the operations further comprise updating the deformation data using the connectivity model.

14. The system of claim 10, wherein the first and second intraocular pressure correspond to a fluid pressure in an aqueous humor of the eye.

15. The system of claim 10, wherein the operations further comprise generating a strain and connectivity model using the colocalized connectivity model and deformation map.

16. The system of claim 15, wherein the retinal blood perfusion is predicted using the colocalized connectivity model and deformation map or the strain and connectivity model.

17. The system of claim 16, wherein the operations further comprise determining a diagnosis, wherein determining a diagnosis comprises using the colocalized connectivity model and deformation map or the strain and connectivity model.

18. The system of claim 17, wherein determining the diagnosis further comprises applying historical data to the colocalized connectivity model and deformation map or the strain and connectivity model.

* * * * *